United States Patent
Shi et al.

(10) Patent No.: US 11,584,948 B2
(45) Date of Patent: Feb. 21, 2023

(54) QUANTITATIVE DETECTION METHOD FOR SNAKE VENOM THROMBIN-LIKE ENZYME (SVTLE)

(71) Applicants: Shandong Institute for Food and Drug Control, Shandong (CN); Shandong University, Shandong (CN); Avanc Pharmaceutical Co., Ltd, Liaoning (CN)

(72) Inventors: Feng Shi, Shandong (CN); Liping Gong, Shandong (CN); Ruiqing Xian, Shandong (CN); Lianli Chi, Shandong (CN); Weijian Wang, Shandong (CN); Baojian Hang, Shandong (CN); Congcong Wang, Shandong (CN); Pengfei You, Shandong (CN); Hongming Du, Liaoning (CN)

(73) Assignees: Shandong Institute for Food and Drug Control, Shandong (CN); Shandong University, Shandong (CN); Avanc Pharmaceutical Co., Ltd, Liaoning (CN)

( * ) Notice: Subject to any disclaimer, the term of this patent is extended or adjusted under 35 U.S.C. 154(b) by 0 days.

(21) Appl. No.: 17/389,384

(22) Filed: Jul. 30, 2021

(65) Prior Publication Data

US 2022/0033873 A1  Feb. 3, 2022

(30) Foreign Application Priority Data

Jul. 30, 2020  (CN) .......................... 202010753044.7

(51) Int. Cl.
*C12Q 1/37*  (2006.01)
*G01N 30/06*  (2006.01)
(Continued)

(52) U.S. Cl.
CPC ............... *C12Q 1/37* (2013.01); *G01N 30/06* (2013.01); *G01N 30/7266* (2013.01);
(Continued)

(58) Field of Classification Search
CPC ............... C12Q 1/37; G01N 2030/027; G01N 2030/067; G01N 2333/96422;
(Continued)

(56) References Cited

U.S. PATENT DOCUMENTS 6,291,247 B1 * 9/2001 Riopelle ................ G01N 33/74
436/2
2002/0064517 A1 * 5/2002 Cederholm-Williams ..................
A61K 48/0041
435/325

FOREIGN PATENT DOCUMENTS

CN   104987363      10/2015
CN   104987363 A  * 10/2015

OTHER PUBLICATIONS

Zeng, Characterization and analysis of a novel glycoprotein from snake venom using liquid chromatography-electrospray mass spectrometry and Edman degradation, 2001, Eur. J. Biochem. 266, 352-358 (Year: 2001).*

* cited by examiner

*Primary Examiner* — John Fitzgerald
*Assistant Examiner* — Truong D Phan
(74) *Attorney, Agent, or Firm* — JCIP Global Inc.

(57) ABSTRACT

The present invention relates to the technical field of chemical analysis and quantitative detection, in particular to a quantitative detection method for snake venom thrombin-like enzyme (SVTLE) from *Agkistrodon halys pallas*. The quantitative detection method for the SVTLE includes the following steps of taking a reference substance of marker peptide for the SVTLE from *Agkistrodon halys pallas* with (Continued)

an amino acid sequence of LDSPVSNSAHIAPLSLPS-SAPSVGSVCR, and preparing a series of reference solutions with different concentrations; adding the reference solutions in test solutions respectively for enzymolysis, and then taking a supernatant after enzymolysis as a series of solutions to be detected; and adding the solutions to be detected in a liquid chromatogram-mass spectrometer, and then selecting a qualitative ion pair and a quantitative ion pair to detect contents of marker peptide in the solutions to be detected.

5 Claims, 8 Drawing Sheets

Specification includes a Sequence Listing.

(51) Int. Cl.
*G01N 30/72* (2006.01)
*G01N 30/86* (2006.01)
*G01N 30/02* (2006.01)

(52) U.S. Cl.
CPC ... *G01N 30/8624* (2013.01); *G01N 2030/027* (2013.01); *G01N 2030/067* (2013.01); *G01N 2333/96422* (2013.01)

(58) Field of Classification Search
CPC .............. G01N 30/06; G01N 30/7266; G01N 30/8624; G01N 33/6848; G01N 2333/4613
See application file for complete search history.

QUANTITATIVE DETECTION METHOD FOR SNAKE VENOM THROMBIN-LIKE ENZYME (SVTLE)

CROSS-REFERENCE TO RELATED APPLICATION

This application claims the priority benefit of China application serial no. 202010753044.7, filed on Jul. 30, 2020. The entirety of the above-mentioned patent application is hereby incorporated by reference herein and made a part of this specification.

BACKGROUND

Technical Field

The present invention relates to the technical field of chemical analysis and quantitative testing, in particular to a quantitative detection method for snake venom thrombin-like enzyme (SVTLE).

Description of Related Art

SVTLE refers to glycoprotein extracted from snack venom, which has the effects of lowering plasma fibrinogen and blood viscosity and the like and has been applied as drugs to treat thrombotic diseases for more than 50 years. In clinical practice, in addition to treating cerebral embolism, thromboangiitis obliterans, femoral artery embolization, pulmonary embolism and other thrombotic diseases and preventing postoperative thrombosis relapse, the SVTLE is also effective in treating nephrosis, lupus erythematosus, viral hepatitis and Raynaud's disease, etc.

As unique *Agkistrodon halys* in China, *Agkistrodon halys pallas* is mainly distributed in Changbai Mountain Area in the northeast and has complicated venom components, including various proteins, polypeptide, nucleoside, enzymes, metal ion and other small molecules. Snake venom thrombin may be obtained by extracting the venom, as raw material, of *Agkistrodon halys pallas*, has the main active ingredients of thrombin-like enzyme contains a few thrombokinase, L-amino oxidase, phosphatase, hyaluronidase, etc. and is clinically widely applied to treating various bleeding and bleeding diseases. Currently reported methods for determining the content of the thrombin-like enzyme in venom mainly include pulsed field gel electrophoresis and efficacy testing method, which are complicated and are poor in accuracy so as not to accurately characterize the mass of venom. Thus, establishment of a convenient and rapid method for detecting the thrombin-like enzyme with accurate quantification to characterize the mass of the venom of *Agkistrodon halys pallas* and a venom extract has wide social benefits and economic effects.

SUMMARY

Aiming at the above problems, the present invention provides a method for detecting a content of thrombin-like enzyme in venom of *Agkistrodon halys pallas* and a venom extract. By using a liquid chromatogram-mass spectrometer and employing a standard addition method to determine the content of the thrombin-like enzyme in venom of *Agkistrodon halys pallas* and a venom extract, the method is simple, convenient and rapid, is less in matrix interference, high in sensitivity and accurate in quantification, fills the gap in the quality standard for the venom of *Agkistrodon halys pallas* and the venom extract and improves the quality control level.

To achieve the above inventive objective, the present invention employs the following technical solution:

a quantitative detection method for snake venom thrombin-like enzyme (SVTLE) includes the steps of:

(1) taking a reference substance of marker peptide for SVTLE from *Agkistrodon halys pallas* with an amino acid sequence of LDSPVSNSAHIAPLSLPSSAPSVGSVCR, and dissolving and diluting the reference substance to prepare a series of reference solutions with different concentrations; (2) taking a suitable quantity of a to-be-detected sample, and dissolving the to-be-detected sample to prepare a test solution; (3) taking the series of reference solutions with different concentrations in step (1), adding the test solutions in step (2) respectively for uniform mixing, conducting enzymolysis with trypsin, and then taking supernatants after enzymolysis as a series of solutions to be detected; (4) injecting the solutions to be detected in step (3) into a liquid chromatogram-mass spectrometer respectively, conducting multiple-reaction monitoring by adopting an electrospray positive ion mode, and conducting detection with tricharged 935.8→602.3 as a qualitative ion pair and tricharged 935.8→861.4 as a quantitative ion pair; and (5) extracting an ion pair tricharged 935.8→861.4 chromatogram, calculating a linear regression equation $y=ax+b$ ($r>0.99$) with an addition quantity of marker peptide in the series of solutions to be detected as a horizontal coordinate and a corresponding peak area as a vertical coordinate, and then calculating an x value when $y=0$ according to the regression equation to obtain the quantity of the marker peptide in the solutions to be detected, and then calculating contents of marker peptide of the SVTLE from *Agkistrodon halys pallas* in the solutions to be detected.

Further, the limit of detection and the limit of quantification for marker peptide of the SVTLE from *Agkistrodon halys pallas* are 3 ng/mL and 9 ng/mL respectively.

Preferably, step (1) includes the following specific operation steps of: weighing 10 mg of the reference substance of the marker peptide of the SVTLE from *Agkistrodon halys pallas*, dissolving the reference substance with 25 mmol/L ammonium bicarbonate solution, diluting the reference substance to 10 mL, and then diluting the reference solution with suitable volumes of the ammonium bicarbonate solutions into a series of reference solutions with concentrations of 0 μg/mL, 0.05 μg/mL, 0.15 μg/mL, 0.3 μg/mL and 0.45 μg/mL respectively.

Preferably, step (2) includes the following specific operation steps of: weighing 20 mg of venom powder or 500 μL of a venom extract of *Agkistrodon halys pallas*, dissolving the venom powder or the venom extract with 25 mmol/L ammonium bicarbonate solution and diluting the venom powder or the venom extract to 10 mL to prepare a test solution;

Preferably, step (3) includes the following specific operation steps of s: weighing 100 μL of test solutions in 5 copies, adding 100 μL of a series of reference solutions with the concentrations of 0 μg/mL, 0.05 μg/mL, 0.15 μg/mL, 0.3 μg/mL and 0.45 μg/mL in the test solutions respectively for uniform mixing, adding 10 μL of 0.2 mol/L DTT solution for uniform mixing, conducting reaction 1 h at 60° C., adding 20 μL of a 0.2 mol/L iodoacetamide solution, placing a product in the dark for 30 min, adding 760 μL of the 25 mmol/L ammonium bicarbonate solution and 10 μL of a 0.4 mg/mL trypsin solution for a reaction for 90 min at 37° C. and inactivation for 10 min at 90° C. respectively, letting products to cool to a room temperature, conducting centrifugation for 10 min at 1200 rpm, and taking supernatants as the series of solutions to be detected.

Preferably, the liquid phase and mass spectrum detection conditions in the liquid chromatogram-mass spectrometer are as follows:

Liquid phase conditions: Waters ACQUITY UPLC BEH $C_{18}$ chromatographic column 50 mm×2.1 mm, 1.7 μm; column temperature: 40° C.; sample size: 2 μL; flow rate: 0.2 mL/min; 0.1% formic acid solution and 0.1% formic acid acetonitrile as mobile phase A, and B respectively for gradient elution as per the procedure: 0→1 min, mobile phase A 80%; 1→5 min, mobile phase A 80%→10%; 5→7 min, mobile phase A 10%→10%.

Mass spectrum conditions: ESI source, positive ion scanning mode, multiple-reaction monitoring; eddy ion spraying temperature: 500° C.; deionization voltage: 5.5 kV; exit potential of a collision chamber: 10 V; entrance potential (EP): 10 V, declustering potential (DP): 135 V; and by mass-to-charge ratio (m/z), tricharged 935.8→602.3 is taken as the qualitative ion pair with collision energy of 40 V, and tricharged 935.8→861.4 is taken as the quantitative ion pair with collision energy of 45 V.

The present invention has the following beneficial effects that:

(1) the present invention conducts library searching and comparison after integrating a protein library and a venom protein library of current snack species by using NCBI and UniProt and finds out marker peptide LDSPVSNSA-HIAPLSLPSSAPSVGSVCR of the SVTLE from *Agkistrodon halys pallas* by combining with large experimental researches. Since it has been known that amino acid sequences of SVTLE from other snake species, including *Bothrops atrox, Vipera russelli siamensis* and *Agkistrodon acutus* do not contain this fragment of amino acid sequence, the marker peptide may be used for specifically characterizing thrombin-like enzyme in the venom of *Agkistrodon halys pallas*.

(2) The present invention establishes a method for detecting a content of trombin-like enzyme in the venom from *Agkistrodon halys pallas* and a venom extract by treating a sample with enzymolysis and using a liquid chromatogram-mass spectrometer. By adopting a standard addition method, the method may lower matrix interference effectively, and is simple, convenient and rapid, is accurate in quantification, fills the gap in the quality standard for the venom of *Agkistrodon halys pallas* and the venom extract and improves the quality control level.

DESCRIPTION OF THE EMBODIMENTS

The present invention will be further described below in combination with specific embodiments:

Preparation methods for relevant reagents and solutions in the following embodiments are as shown below:

(1) Reagent: trypsin (Sigma, Batch No.: SLBS8956), snake venom thrombin of *Agkistrodon halys pallas* (Avanc Pharmaceutical Co., Ltd., Purity: 98.5%), guanidine hydrochloride (VETEC, Batch No.: WXBC4261V), tromethamine (Shanghai, Batch No.: 20181206), dithiothreitol (BBI Life Sciences, Batch No.: D911BA0011), iodoacetamide (BBI Life Sciences, Batch No.: B326BA1943), while other reagents are all analytically pure.

(2) 25 mmol/L ammonium bicarbonate solution: weighing 79.06 mg of ammonium bicarbonate, and then dissolving the ammonium bicarbonate with 40 mL of water to obtain the solution.

(3) Dithiothreitol (DTT) solution: weighing 15.42 mg of dithiothreitol, and then dissolving the dithiothreitol 500 μL of water to obtain the solution.

(4) Iodoacetamide (IA) solution (which is newly prepared upon use): weighing 18.5 mg of iodoacetamide, and then dissolving the iodoacetamide with 500 μL of water to obtain the solution.

(5) 0.4 mg/mL trypsin solution (which is newly prepared upon use): weighing 8.0 mg of trypsin, and then dissolving the trypsin with 20 mL of water to obtain the solution.

Embodiment 1

Screening and confirmation of marker peptide for SVTLE from *Agkistrodon halys pallas*.

1. Instrument and Equipment

Thermo Fusion high resolution mass spectrometer (Thermo Fisher Scientific, America), EASY-nLC 1000 nL liquid chromatograph (Thermo Fisher Scientific, America), CP225D electronic scales (Sartorius, Germany), Sigma 3-30 K refrigerated centrifuge (Sigma, Germany), Millipore Milli-QAdvantage A10 Ultra-Pure Water Purifier (Millipore, America)

2. Mass Spectrum Conditions of Chromatography

Chromatographic column: desalting and enrichment were conducted by using a 0.2 mm×3.5 cm (5 μm particle size) ReproSil-Pur Cis-AQ Trap column made in the laboratory, and 75 μm×25 cm (3 μm particle size) ReproSil-Pur C18-AQ nanoliter analytical column made in the laboratory was employed for separation. A mobile phase A is a 0.1% formic acid solution of 2% acetonitrile, while a mobile phase B is a 0.1% formic acid solution of 98% acetonitrile. The flow rate of nanoliter separation pump is 300 nL/min, and gradient elution settings are as shown in Table 1 below.

TABLE 1

| List of Gradient Elution for Nanoliter Liquid Phase- High Resolution Mass Spectrum | | |
| --- | --- | --- |
| Time (min) | Mobile Phase A(nL/min) | Mobile Phase B(nL/min) |
| 0 | 300 | 0 |
| 3 | 300 | 0 |
| 5 | 300 | 0 |
| 20 | 270 | 30 |
| 75 | 204 | 96 |

TABLE 1-continued

List of Gradient Elution for Nanoliter Liquid Phase- High Resolution Mass Spectrum

| Time (min) | Mobile Phase A(nL/min) | Mobile Phase B(nL/min) |
|---|---|---|
| 95 | 150 | 150 |
| 100 | 0 | 300 |
| 100.5 | 0 | 450 |
| 108 | 0 | 450 |
| 110 | 450 | 0 |
| 115 | 450 | 0 |
| 120 | 450 | 0 |

Mass spectrum conditions: a positive ion mode was employed for analysis, wherein the spray voltage was 2.0 kV, a temperature of an ion transport capillary was 275° C., and the transmission efficiency of S-Lens was set as 60%. Orbitrap was taken as a mass analyzer for a primary mass spectrum, wherein a resolution ratio was 60,000, and a collection scope v 350-1650. IT was taken as a mass analyzer for a secondary mass spectrum, and a Rapid Scan mode was employed for scanning, a Top20 data dependence mode is employed for parent ion selection, and an HCD mode was employed for fracturing, wherein the fracturing energy NCE was set as 35%.

3. Data Collection 5 mg of SVTLE from *Agkistrodon halys pallas* was put in a 10 mL measuring flask and was dissolved with 25 mmol/L ammonium bicarbonate solution to a constant volume; 200 μL of the solution was precisely measured, 10 μL of a 0.2 mol/L dithiothreitol solution was added, a mixture was blended uniformly and reacted for 1 h at 60° C., 20 μL of a 0.2 mol/L iodoacetamide solution was added, a mixture was placed in the dark for 30 min, 760 μL of the 25 mmol/L ammonium bicarbonate solution and 10 μL of a 0.4 mg/mL trypsin solution (which was newly prepared upon use) were added, the mixture was reacted for 90 min at 37° C. and inactivated for 10 min at 90° C., then cooled to a room temperature, and centrifugation was conducted for 10 min at 1200 rpm, supernatant was taken as a test solution that is injected via nanoliter liquid separation, and the primary mass spectrum and the secondary mass spectrum were collected by using a high resolution mass spectrum.

4. Screening and Confirmation with Library Searching

Figure 1:
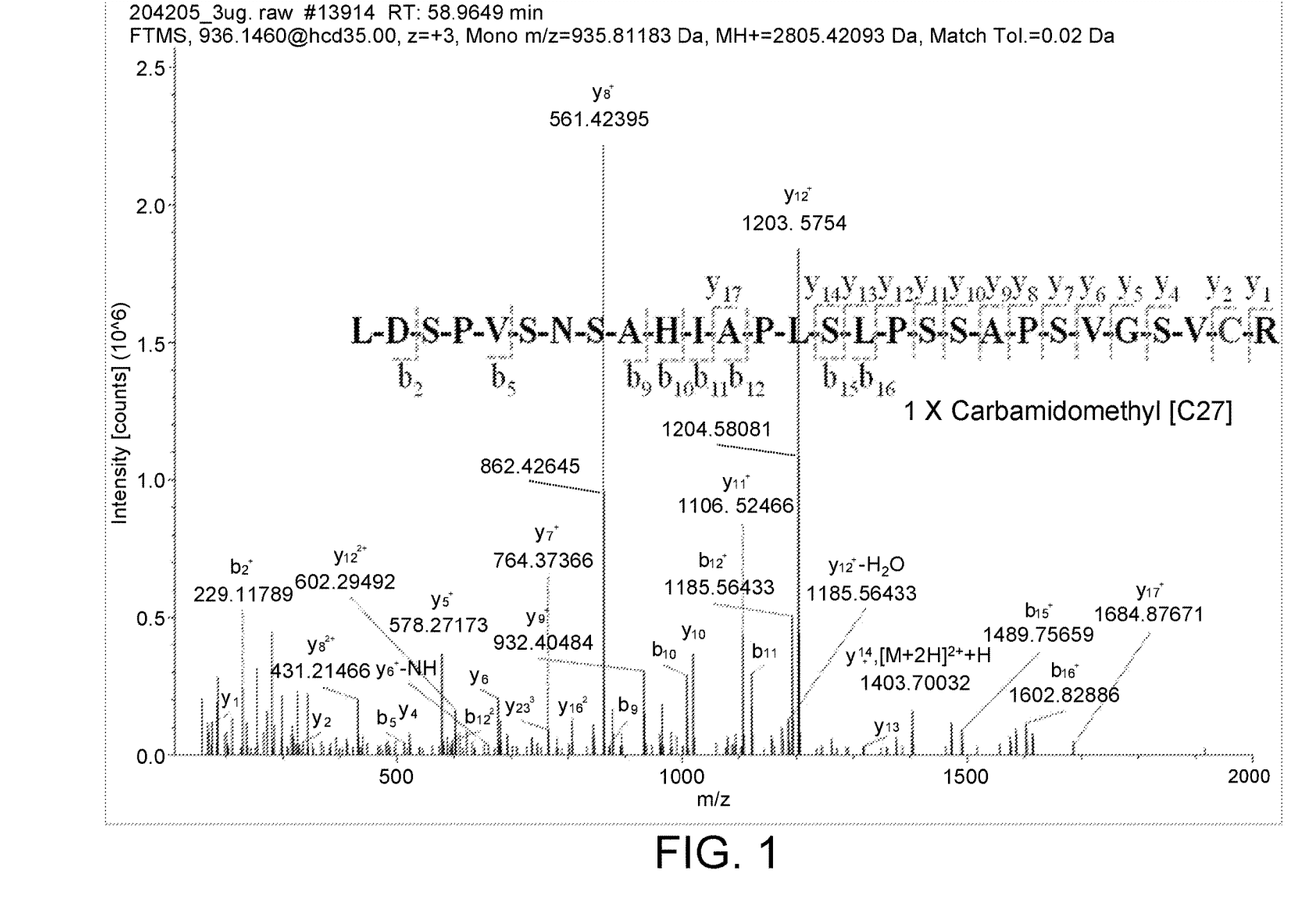
FIG. 1 shows a tandem mass spectrogram spectra of marker peptide for snake venom thrombin-like enzymes from *Agkistrodon halys pallas*.
Figure 2:
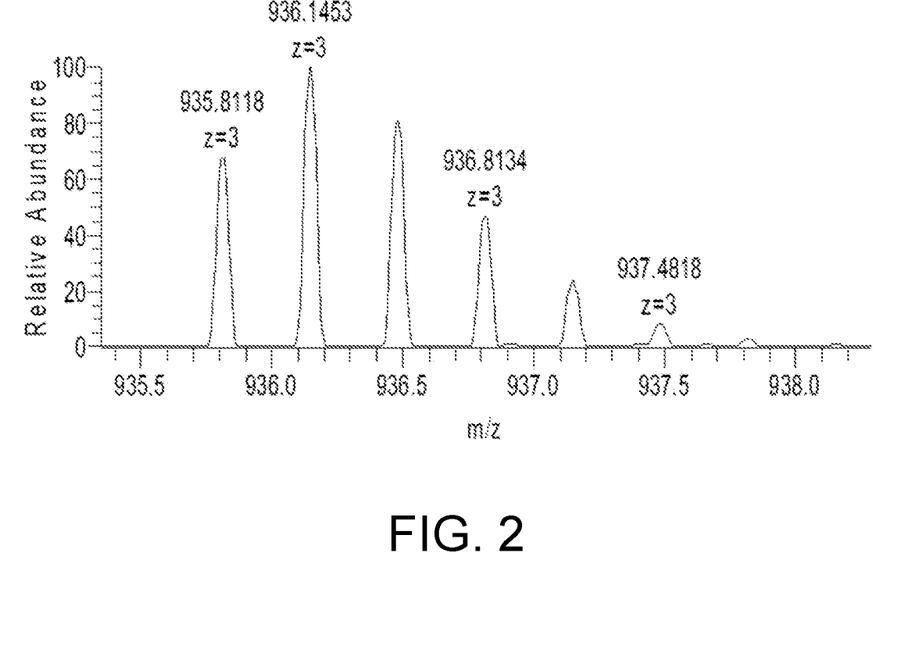
FIG. 2 shows a mass spectrogram spectra of marker peptide for snake venom thrombin-like enzymes from *Agkistrodon halys pallas*.

NCBI and UniProt were applied to integrate the relevant snack protein library and venom protein library, and then a snack and venom database was established. Based on a Peptidemass function provided by the UniProt, results of enzymatically hydrolysing SVTLE proteins of different species with the trypsin was simulated, and a sequence of the marker polypeptide of *Agkistrodon halys pallas* relative to other species was obtained by comparing a protein sequence of thrombin-like enzyme from *Agkistrodon halys pallas* with that in other species, a mass spectrum database was searched by using Proteome Discoverer Software (Version 2.2), and "LDSPVSNSAHIAPLSLPSSAPSVGSVCR" was confirmed as the marker peptide of the SVTLE from *Agkistrodon halys pallas* by referring to the principles of (1) 8-25 amino acids; (2) avoiding peptide fragments that readily undergoes artificial modification as much as possible, and (3) no omission of restriction site in digestion, etc. According to the detection result, the molecular weight and the secondary mass spectrum of marker peptide are in consistence with theoretical values, as shown in FIG. 1 and FIG. 2.

Embodiment 2

SVTLE from *Agkistrodon halys pallas* in multiple-reaction monitoring (MRM) quantitative analysis samples 1. Instrument and Equipment SCIEX Triple Quad 6500 Mass Spectrometer, CP225D Electronic Scales (Sartorius, Germany), Sigma 3-30 K Refrigerated Centrifuger (Sigma, Germany), Milli-QAdvantage A10 UP Water Purification System (Millipore, America).

2. Mass Spectrum Conditions of Chromatography

Liquid phase conditions: Waters ACQUITY UPLC BEH $C_{18}$ chromatographic column (50 mm×2.1 mm, 1.7 μm); column temperature: 40° C.; sample size: 2 μL; flow rate: 0.2 mL/min; and a mobile phase A is 0.1% formic acid solution and a mobile phase B is 0.1% formic acid acetonitrile for gradient elution, wherein the elution procedure is as follows: 0→1 min, mobile phase A 80%; 1→5 min, mobile phase A 80%→10%; 5→7 min, mobile phase A 10%→10%.

Mass spectrum conditions: ESI source, positive ion scanning mode, multiple-reaction monitoring; eddy ion spraying temperature: 500° C.; deionization voltage: 5.5 kV; exit potential of a collision chamber: 10 V; entrance potential (EP): 10 V, declustering potential (DP): 135V; and by mass-to-charge ratio (m/z), tricharged 935.8→602.3 was taken as a qualitative ion pair with collision energy of 40 V, and tricharged 935.8→861.4 was taken as a quantitative ion pair with collision energy of 45 V.

3. Solution Preparation 3.1. Preparation of Series of Concentration Reference Solutions 10 mg of reference substance of the marker peptide screened in Embodiment 1 was precisely weighed, put in a 10 mL measuring flask, and dissolved with a 25 mmol/L ammonium bicarbonate solution, and the flask was filled with water to the scale mark, uniform mixing was conducted, 0 μL, 5 μL, 15 μL, 30 μL, 45 μL and 60 μL of mixtures were precisely measured, put in 100 mL measuring flasks and diluted with a 25 mmol/L ammonium bicarbonate solution to prepare a series of reference solutions with concentrations of 0 μg/mL, 0.05 μg/mL, 0.15 μg/mL, 0.30 μg/mL, and 0.45 μg/mL.

3.2. Preparation of Test Solutions

The to-be-detected sample (20 mg of venom powder or 500 μL of a venom extractive of *Agkistrodon halys pallas*) was precisely weighed, put in a 10 mL measuring flask and dissolved with the 25 mmol/L ammonium bicarbonate solution to a constant volume, and uniform mixing was conducted to obtain the test solution.

3.3. Preparation of Series of Solutions to be Detected 5 100 μL of test solutions in Item 3.2 were precisely weighed, 100 μL of the series of reference solutions with different concentrations in Item 3.1 were added respectively for uniform mixing, 10 μL of 0.2 mol/L dithiothreitol solution was added, a mixture was blended uniformly and reacted for 1 h at 60° C., 20 μL of a 0.2 mol/L iodoacetamide solution was added, a mixture was put in the dark for 30 min, 760 μL of the 25 mmol/L ammonium bicarbonate solution and 10 μL of a 0.4 mg/mL trypsin solution (which was newly prepared upon use) were added, the mixture was reacted for 90 min at 37° C. and inactivated for 10 min at 90° C. respectively, then cooled to a room temperature, and centrifugation was conducted for 10 min at 1200 rpm, and supernatants were taken as the series of solutions to be detected.

3.4. Preparation of Blank Solutions to be Detected

200 μL of a 25 mmol/L ammonium bicarbonate solution was precisely weighed, 10 μL of a 0.2 mol/L dithiothreitol solution was added for uniform mixing, a reaction was conducted for 1 h at 60° C., 20 μL of a 0.2 mol/L iodoacetamide solution was added, a mixture was put in the dark for 30 min, 760 μL of the 25 mmol/L ammonium bicarbonate solution and 10 μL of a 0.4 mg/mL trypsin solution (which was newly prepared upon use) were added for a reaction 90 min at 37° C. and inactivation for 10 min at 90° C., the mixture was cooled to the room temperature, centrifugation was conducted for 10 min at 1200 rpm, and a supernatant was taken as a blank solution.

4. Assay Method

2 μL of the above series of solutions to the detected were taken, detection was conducted according to the chromatography-mass spectrum conditions in Item 2, an ion tricharged 935.8→861.4 chromatogram was extracted, a linear regression equation y=ax+b, (r>0.99) was calculated with an addition quantity of the marker peptide in the series of solutions to be detected as a horizontal coordinate and a corresponding peak area as a vertical coordinate of an x value when y=0 was calculated according to the regression equation to obtain the contents of the marker peptide in the solutions to be detected, and then the content of the marker peptide of the thrombin-like enzyme in the to-be-detected sample was calculated.

5. Specificity

Figure 3:
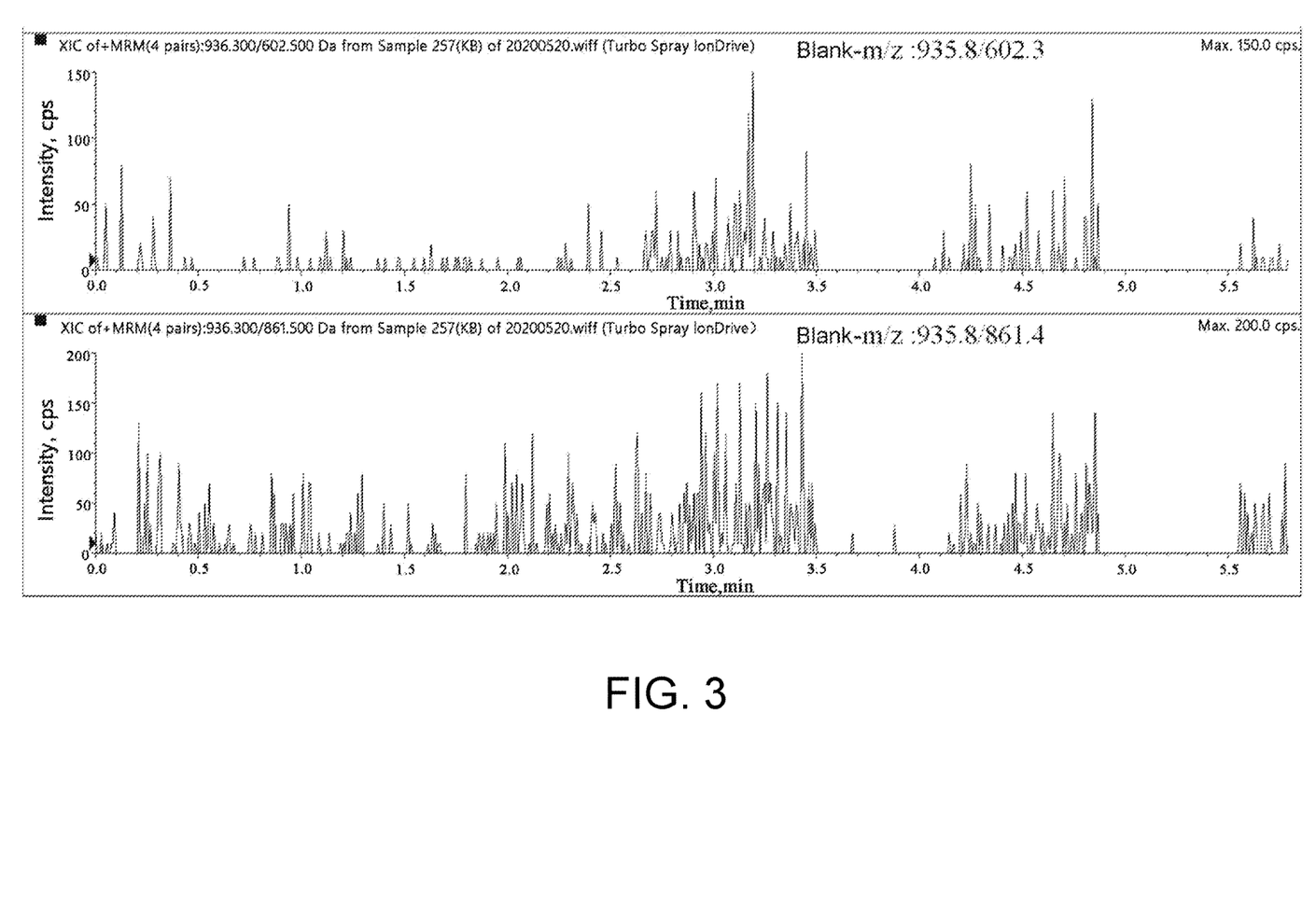
FIG. 3 shows an investigation of specificity map-blank solution mass spectrogram.

2 μL of the test solution, 2 μL of the blank solution and 2 μL of the reference solution were taken respectively for liquid quality analysis, and results showed that, the blank solution had no interference peak at the position that a peak appeared of the reference solution, while the test solution had a responded chromatographic peak at the position that a peak appeared of the reference solution, indicating that the method was good in specificity, as shown in FIGS. 1-3.

Figure 4:
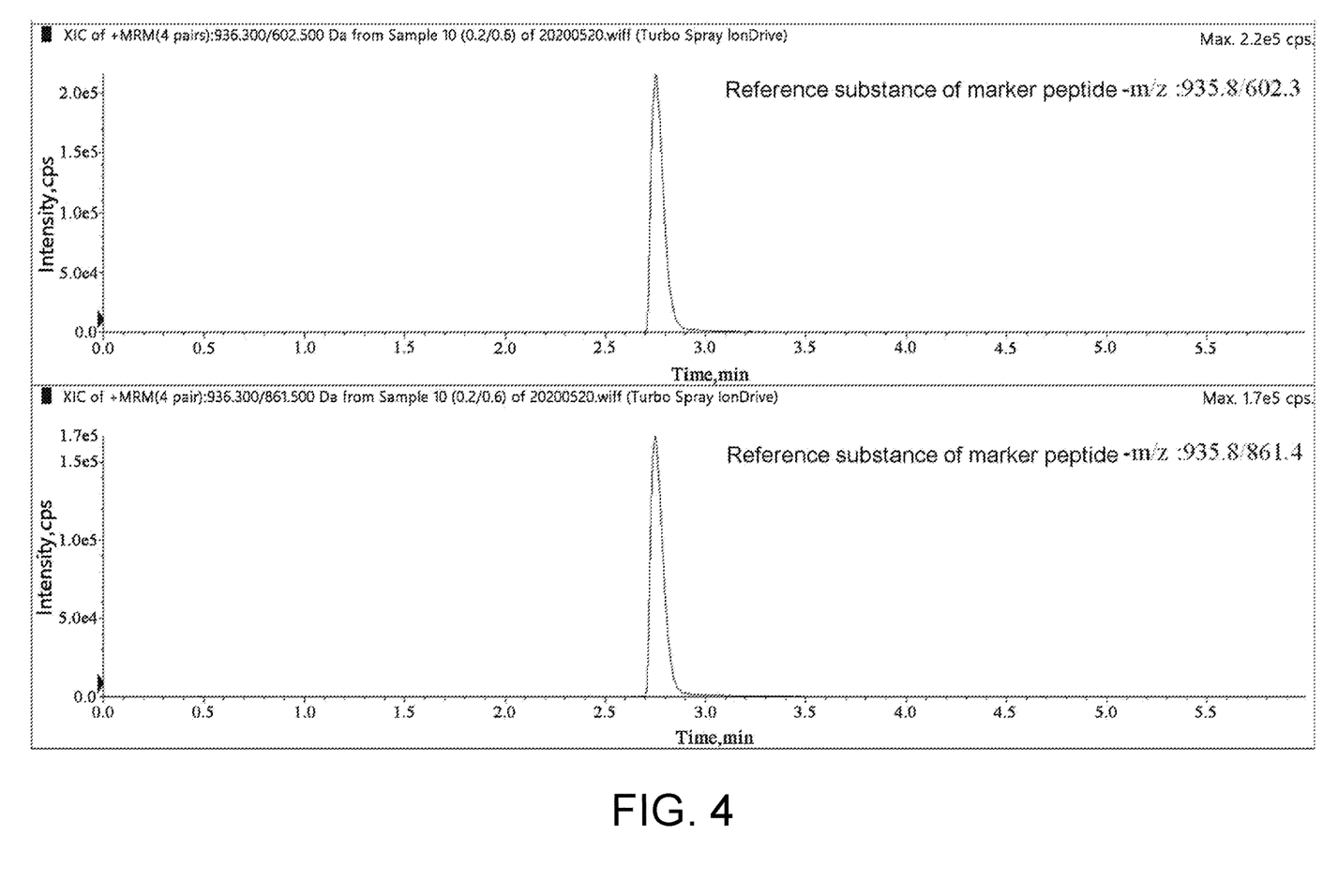
FIG. 4 shows an investigation of specificity map-marker peptide reference quality mass spectrogram.
Figure 5:
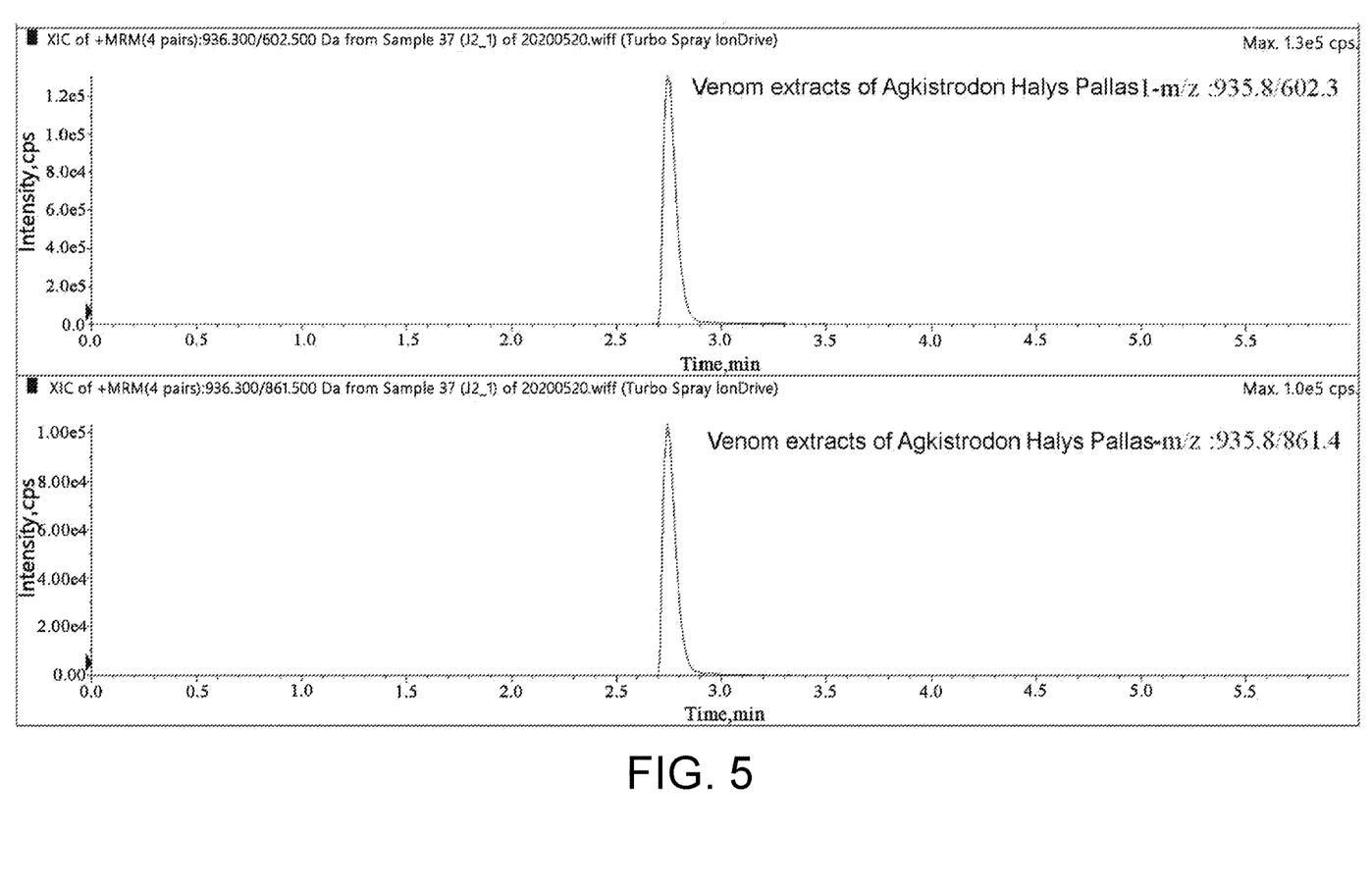
FIG. 5 shows an investigation of specificity map-*Agkistrodon halys pallas* venom extract 1 mass spectrogram.
Figure 6:
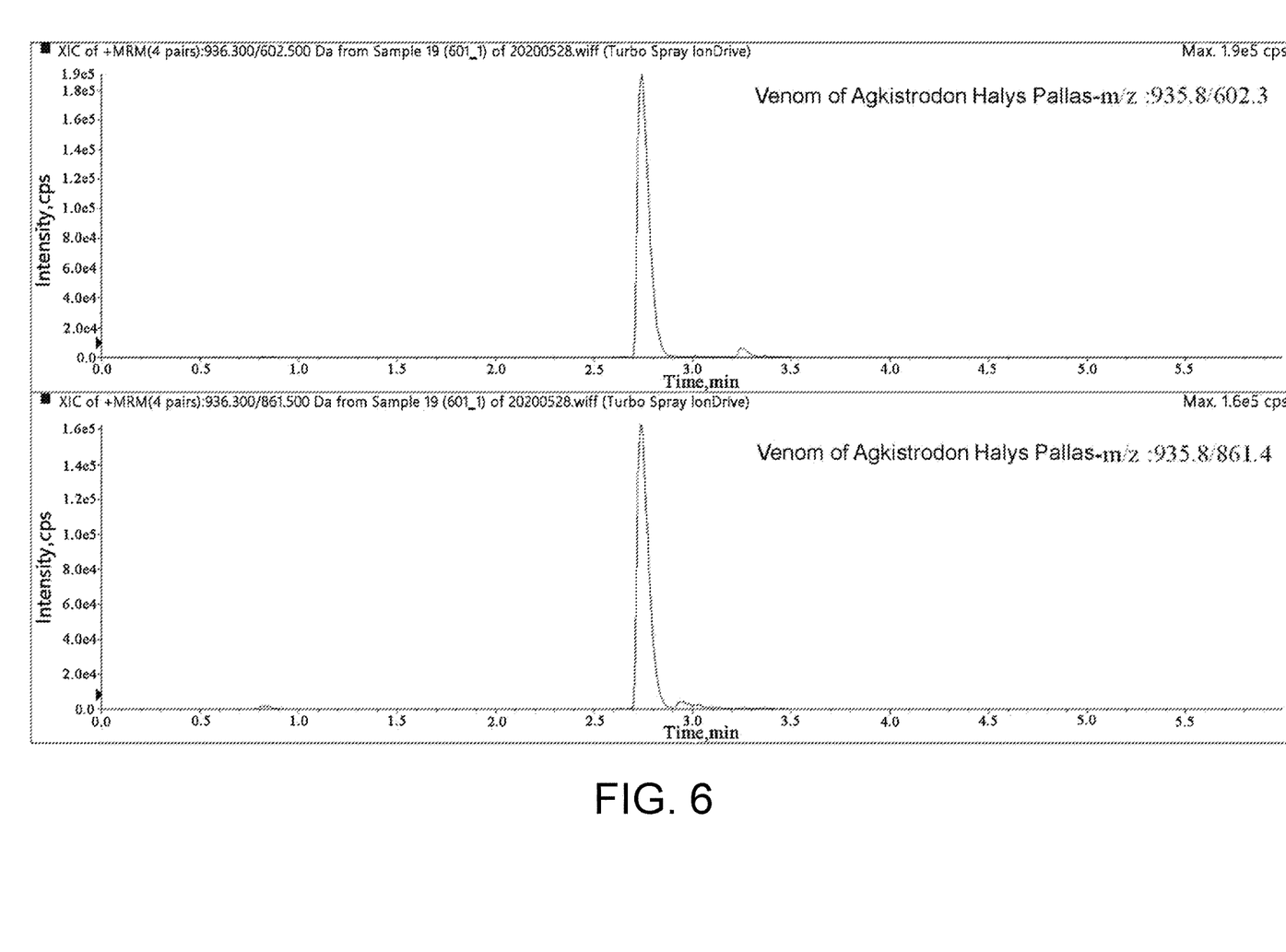
FIG. 6 shows an investigation of specificity map-*Agkistrodon halys pallas* venom mass spectrogram.
Figure 7:
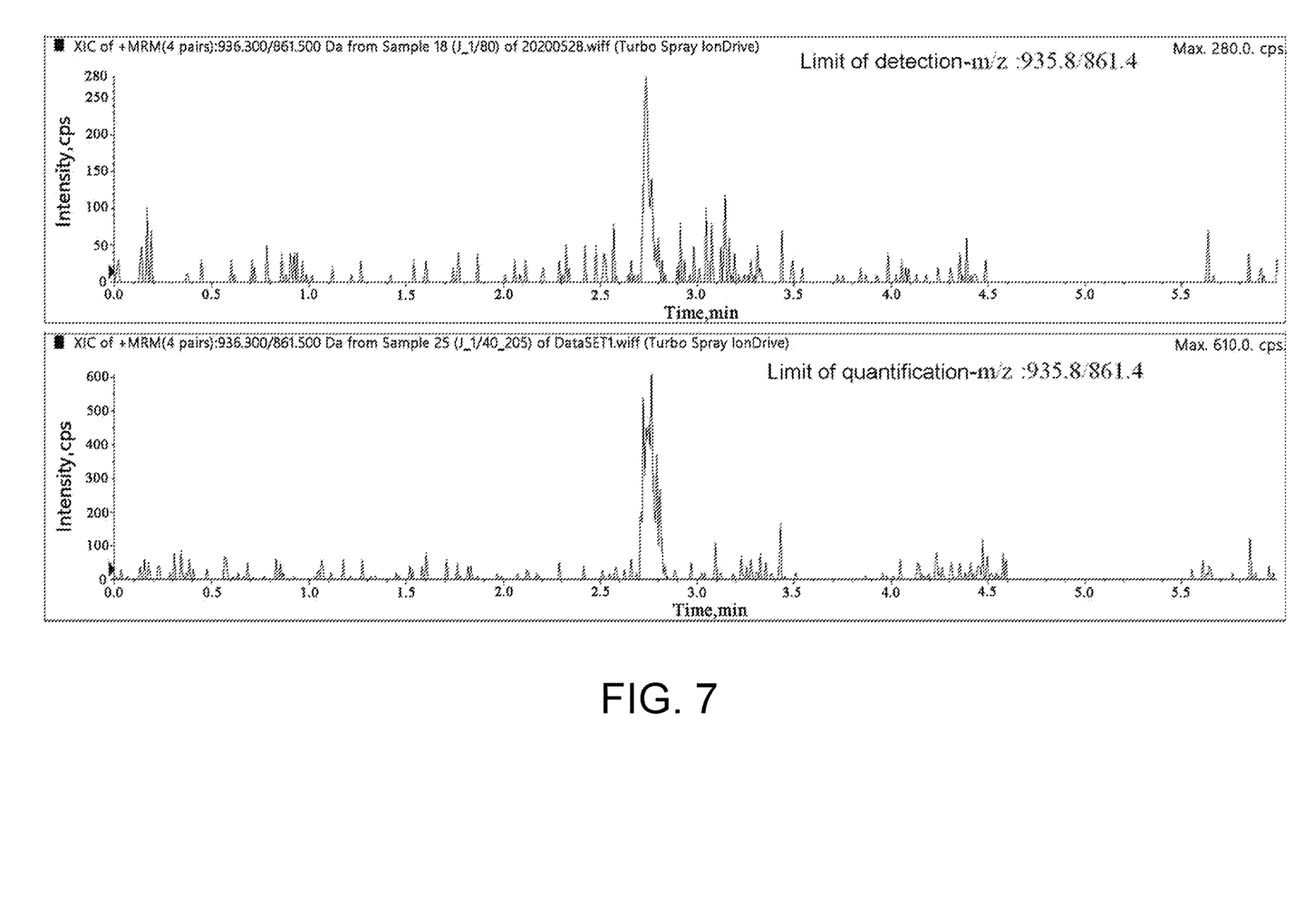
FIG. 7 shows a mass spectrogram for a limit of detection and a limit of quantification.
Figure 8:
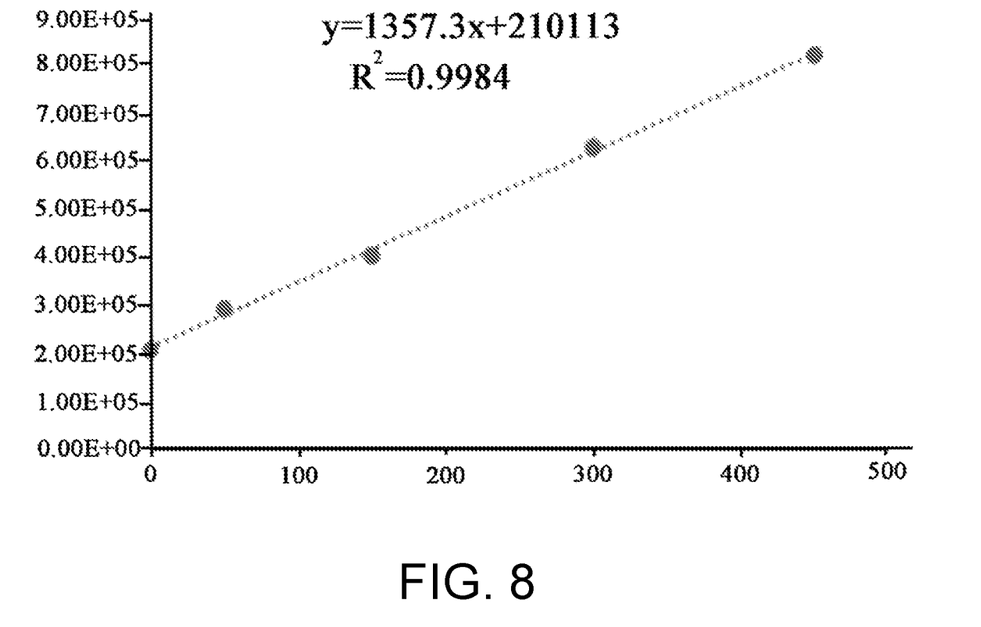
FIG. 8 shows a linearity and range map.

6. Limit of Detection and Limit of Quantification 0.15 μg/mL of the reference solution was taken for enzymolysis according to Item 3.3 and was diluted to concentrations of 3 ng/mL and 9 ng/mL respectively for sample injection with the quantity of 2 μL, and detection was conducted with tricharged 935.8→861.4 of the marker peptide as the quantitative ion pair, wherein the signal-to-noise ratios were 3.1 and 9.8 respectively. Thus, the limit of detection and limit of quantification were 3 ng/mL and 9 ng/mL respectively, as shown in FIG. 4.

7. Linearity and Repeatability

500 μL of venom extracts of *Agkistrodon halys pallas* (Batch No.: 20190201) were taken according to Item 3.2, 6 test solutions were prepared, and a series of solutions to be detected were prepared according to 3.3 respectively, and detection was conducted. The result indicated that, within the addition quantity of the marker peptide from 0 ng to 450 ng, the concentration of the marker peptide was of linear relation with a chromatographic peak area, and all relevant coefficients were larger than 0.99. In 6 repeated tests, an average content of the marker peptide in the samples was 31.5 μg/mL, RSD % was 3.7%, and the repeatability was excellent.

TABLE 2

| No. | Standard Curve | Correlation Coefficient r | Content (μg/mL) | RSD |
|---|---|---|---|---|
| 1 | y = 1311.8x + 202967 | 0.9961 | 30.9 | 3.7% |
| 2 | y = 1357.3x + 210113 | 0.9992 | 31.0 | |

TABLE 2-continued

| No. | Standard Curve | Correlation Coefficient r | Content (μg/mL) | RSD |
|---|---|---|---|---|
| 3 | y = 1366.1x + 208635 | 0.9990 | 30.5 | |
| 4 | y = 1337.8x + 212323 | 0.9952 | 31.7 | |
| 5 | y = 1326.9x + 223682 | 0.9994 | 33.7 | |
| 6 | y = 1346.6x + 208755 | 0.9971 | 31.0 | |

8. Precision

The solution to be detected (with the addition quantity of the reference substance of 300 ng) in Item 3.3 was taken, the sample was injected continuously and repeatedly for 6 times, a tricharged 936.3→861.4 ion pair chromatogram was extracted, showing that a peak area RSD of sample injection for 6 times was 1.8%, and the precision of an instrument was excellent.

9. Stability

The solution to be detected (with the addition quantity of the reference substance of 150 ng) in Item 3.3 was taken, put at 8° C. after being treated and determined with sample injection after 0 h, 2 h, 4 h, 8 h, 16 h and 24 h respectively, a tricharged 935.8→861.4 ion pair chromatogram was extracted, and a peak area RSD was 0.9%, indicating that the solution to be detected was stable within 24 h at 8° C.

TABLE 3

| Time (h) | Peak Area | Average Value | RSD |
|---|---|---|---|
| 0 | 4.20E+05 | 4.23E+05 | 0.90% |
| 2 | 4.21E+05 | | |
| 4 | 4.25E+05 | | |
| 8 | 4.25E+05 | | |
| 16 | 4.17E+05 | | |
| 24 | 4.27E+05 | | |

10. Sample Detection

The venom of *Agkistrodon halys pallas* and a venom extract, venom of *Bothrops atrox* and venom powder of unknown snack species were treated according to the method in Item 3 and then detected according to the method in Item 4. Results were shown in Table 4, and the contents are similar for different batches.

TABLE 4

| Sample Name | Batch No. | Content |
|---|---|---|
| Venom of *Agkistrodon Halys Pallas* | 20180601F | 0.98 μg/mg |
| | 20180702F | 1.02 μg/mg |
| | 20170802 | 1.04 μg/mg |
| Venom extracts of *Agkistrodon Halys Pallas* | 20190201 | 31.5 μg/mL |
| Venom extracts of *Agkistrodon Halys Pallas* | 20190202 | 32.3 μg/mL |
| Venom extracts of *Agkistrodon Halys Pallas* | 20190203 | 32.6 μg/mL |
| Venom of *Bothrops atrox* | 2004171 | Not detected |
| Venom of *Bothrops atrox* | 2004172 | Not detected |
| Venom powder | 20200304 | Not detected |
| Venom powder | 20200405 | Not detected |

The above embodiments are preferred implementations of the present invention, but the implementations of the present invention are not limited by the embodiments. Any other changes, modifications, combinations, replacement and simplification made in accordance with the essential spirit and principle of the present invention shall be considered as an equivalent mode of replacement, and are included in the protection range of the present invention.

What is claimed is:

1. A quantitative detection method for snake venom thrombin-like enzyme (SVTLE), comprising the following specific steps of:
  (1) taking a reference substance of a marker peptide for SVTLE from *Agkistrodon halys pallas* with an amino acid sequence of LDSPVSNSAHIAPLSLPSSAPSVGSVCR, and dissolving and diluting the reference substance to prepare a series of reference solutions with different concentrations;
  (2) taking a to-be-detected sample, and dissolving the to-be-detected sample to prepare a test solution;
  (3) taking the series of reference solutions with different concentrations in step (1), adding the test solutions in step (2) respectively for uniform mixing, conducting enzymolysis with trypsin, and then taking supernatants after enzymolysis as a series of solutions to be detected;
  (4) injecting the solutions to be detected in step (3) into a liquid chromatogram-mass spectrometer respectively, conducting multiple-reaction monitoring by adopting an electrospray positive ion mode with tricharged ion m/z 935.8 to 602.3 as a qualitative ion pair and tricharged ion m/z 935.8 to 861.4 as a quantitative ion pair; and
  (5) extracting an ion pair tricharged 935.8 to 861.4 chromatogram, calculating a linear regression equation y=ax+b (r>0.99) with an addition quantity of the marker peptide in the series of solutions to be detected as a horizontal coordinate and a corresponding peak area as a vertical coordinate, and then calculating an x value when y=0 according to the regression equation to obtain the quantity of the marker peptide in the solutions to be detected, and then calculating contents of the marker peptide of the SVTLE from *Agkistrodon halys pallas* in the solutions to be detected;
  wherein liquid phase and mass spectrum detection conditions in the liquid chromatogram-mass spectrometer are as follows:
  the Liquid phase conditions: Waters ACQUITY UPLC BEH $C_{18}$ chromatographic column: 50 mm×2.1 mm, 1.7 µm particle size; column temperature: 40° C.; sample size: 2 µL; flow rate: 0.2 mL/min; a mobile phase A is 0.1% formic acid solution and a mobile phase B is 0.1% formic acid acetonitrile for gradient elution, a elution procedure of which is as follows: 0→1 min, the mobile phase A 80%; 1→5 min, the mobile phase A 80%→10%; 5→7 min, the mobile phase A 10%→10%; and
  the Mass spectrum conditions: ESI source, positive ion scanning mode, multiple-reaction monitoring; eddy ion spraying temperature: 500° C.; deionization voltage: 5.5 kV; exit potential of a collision chamber: 10 V; entrance potential (EP): 10 V, declustering potential (DP): 135 V; and by mass-to-charge ratio (m/z), tricharged 935.8→602.3 is taken as the qualitative ion pair with collision energy of 40 V, and tricharged 935.8→861.4 is taken as the quantitative ion pair with collision energy of 45 V.

2. The method according to claim 1, wherein a limit of detection for the marker peptide of the SVTLE from *Agkistrodon halys pallas* is 3 ng/mL, while a limit of quantification is 9 ng/mL.

3. The method according to claim 1, wherein the step (1) comprises the following specific operation steps of weighing 10 mg of the reference substance of the marker peptide of the SVTLE from *Agkistrodon halys pallas*, dissolving the reference substance with 25 mmol/L ammonium bicarbonate solution, diluting the reference substance to 10 mL, and then diluting the reference solution with the ammonium bicarbonate solution into the series of reference solutions with concentrations of 0 µg/mL, 0.05 µg/mL, 0.15 µg/mL, 0.3 µg/mL and 0.45 µg/mL respectively.

4. The method according to claim 1, wherein the step (2) comprises the following specific operation steps of weighing 20 mg of venom powder or 500 µL of a venom extractive of *Agkistrodon halys pallas*, dissolving the venom powder or the venom extract with 25 mmol/L ammonium bicarbonate solution and diluting the venom powder or the venom extract to 10 mL to prepare the test solution.

5. The method according to claim 1, wherein the step (3) comprises the following specific operation steps of: weighing 100 µL of the test solutions in 5 copies, adding 100 µL of the series of reference solutions with the concentrations of 0 µg/mL, 0.05 µg/mL, 0.15 µg/mL, 0.3 µg/mL and 0.45 µg/mL in the test solutions respectively for uniform mixing, adding 10 µL of a 0.2 mol/L DTT solution for uniform mixing, conducting reaction for 1 h at 60° C., adding 20 µL of a 0.2 mol/L iodoacetamide solution, placing a product in dark for 30 min, adding 760 µL of the 25 mmol/L ammonium bicarbonate solution and 10 µL of a 0.4 mg/mL trypsin solution for a reaction for 90 min at 37° C. and inactivation for 10 min at 90° C. respectively, letting the products to cool to a room temperature, conducting centrifugation for 10 min at 1200 rpm, and taking the supernatants as the series of solutions to be detected.

* * * * *

SEQUENCE LISTING

<160> NUMBER OF SEQ ID NOS: 1

<210> SEQ ID NO 1
<211> LENGTH: 28
<212> TYPE: PRT
<213> ORGANISM: Gloydius ussuriensis

<400> SEQUENCE: 1

Leu Asp Ser Pro Val Ser Asn Ser Ala His Ile Ala Pro Leu Ser Leu
1               5                   10                  15

Pro Ser Ser Ala Pro Ser Val Gly Ser Val Cys Arg
            20                  25